United States Patent [19]

Maciejewski

[11] Patent Number: 5,448,917
[45] Date of Patent: Sep. 12, 1995

[54] APPARATUS FOR CONDUCTING FATIGUE TESTS USING A CONVENTIONAL LATHE DEVICE

[75] Inventor: Wendell C. Maciejewski, Salem, Conn.

[73] Assignee: The United States of America as represented by the Secretary of the Navy, Washington, D.C.

[21] Appl. No.: 399,104

[22] Filed: Mar. 1, 1995

[51] Int. Cl.⁶ ............................................. G01N 3/32
[52] U.S. Cl. ........................................ 73/812; 73/808
[58] Field of Search ................ 73/808, 812, 829, 831, 73/833, 843, 849, 852, 853, 856, 858, 788, 811

[56] References Cited

U.S. PATENT DOCUMENTS

| | | | |
|---|---|---|---|
| 3,214,969 | 11/1965 | Swanson | 73/812 |
| 3,218,848 | 11/1965 | Wahlgren | 73/812 |
| 4,175,447 | 11/1979 | Fukuhara | 73/808 |
| 4,941,359 | 7/1990 | Quinn et al. | 73/851 |
| 5,353,654 | 10/1994 | Lin | 73/808 |

Primary Examiner—Richard Chilcot
Assistant Examiner—Max Noori
Attorney, Agent, or Firm—Michael J. McGowan; Michael F. Oglo; Prithvi C. Lall

[57] ABSTRACT

Apparatus is provided for conducting flexure tests on a rectangular test beam. The apparatus includes a bearing apparatus, a support structure for supporting a beam for deflection, and a deflection guide for flexing the test beam at a predetermined point. The bearing apparatus includes a pintle and a roller bearing axially mounted on a first end of the pintle. The second end of the pintle is mounted in the jaws of the chuck lathe for eccentric rotation of the roller bearing. The support structure includes two locating brackets for supporting the ends of the test beam. The support structure further includes caging apparatus for caging movement of the test beam. The deflection guide is positionable on top of the test beam between the locating brackets, so that a central impeller element faces the upper surface of the test beam. When the bearing makes contact with the deflection guide during eccentric rotation the impeller element engages and flexes the test beam at a mid-point thereof. The supporting and caging structures are constructed and arranged so that the test beam is not constrained along any surface thereof. The apparatus may further include a mechanical cycle counter for counting the revolutions or cycles of the lathe device.

8 Claims, 5 Drawing Sheets

APPARATUS FOR CONDUCTING FATIGUE TESTS USING A CONVENTIONAL LATHE DEVICE

STATEMENT OF GOVERNMENT INTEREST

The invention described herein may be manufactured and used by or for the Government of the United States of America for governmental purposes without payment of any royalties thereon or therefor.

BACKGROUND OF THE INVENTION

1. Field of the Invention

The instant invention relates to fatigue testing machines, and more particularly to apparatus for conducting a beam flexure test on a rectangularly cross-section test beam.

2. Description of the Prior Art

Fatigue testing machines have heretofore been known in the art. In this connection, there are presently available a wide variety of fatigue testing machines. Typically, the commercially available fatigue testing machines utilize a servo-hydraulic type apparatus for flexural movement. In general, the available testing machines are excellent for conducting tests and gathering millions of cycles of data in a relatively short period of time. However, there are some drawbacks to the currently available devices. Most importantly, the machines are expensive to purchase and service. In addition, the various available accessories can be heavy and awkward. Still further, a great majority of the devices require operator training.

There are other less sophisticated testing machines available for special purpose testing. Such machines may include a rotating counterweight or electro-mechanical apparatus for reciprocal movement. While these machines are usually easier to operate, they are also expensive to purchase and service.

Accordingly, among the several objects of the invention are: the provision of a fatigue testing apparatus which is simple to operate and inexpensive to fabricate; the provision of fatigue testing apparatus which uses the rotary movement of a conventional lathe device for cyclical flexure of a rectangularly cross-section test beam; the provision of a bearing apparatus which is mountable in the jaws of a rotatable chuck; the provision of a support structure for supporting a rectangularly cross-section test beam in planar relation with a bearing of the bearing apparatus; the provision of a support structure for capturing and supporting the test beam for conducting a three-point flexure test; and the provision of a flexible deflection guide for imparting a deflective force to a central point on the beam.

SUMMARY OF THE INVENTION

The above objects are accomplished by providing apparatus comprising a bearing apparatus mountable in the jaws of the lathe chuck, a support structure for rigidly supporting the ends of a rectangularly cross-section test beam, a caging apparatus for caging movement of the test beam, and a flexible deflection guide including an impeller element for flexing the test beam at a mid-point thereof. The roller bearing assembly consists of inner and outer races with roller balls positioned in a raceway formed between the inner and outer races. The roller bearing assembly is mounted on the end of a pintle. The pintle is mountable in the jaws of the chuck which are positioned in offset relation for eccentric rotation of the pintle and roller bearing assembly. The support structure includes two locating brackets for supporting the ends of the test beam in normal relation to the plane of rotation of the roller bearing. Two U-shaped guide blocks are mounted on the locating brackets for caging the ends of the test beam, i.e., for preventing horizontal movement of the beam during testing. It is pointed out that the caging apparatus does not rigidly constrain the test beam along any face thereof. The deflection guide is positionable on top of the beam between the locating brackets with the impeller element in confronting relation with the upper surface of the test beam. When the outer race of the roller bearing makes contact with the deflection guide during its eccentric rotation, the impeller element engages the test beam and imparts a downward deflective force to a mid-point of the beam. It is also noted that the deflection guide has a length which is slightly shorter than the distance between the locating brackets and further has a width which is slightly greater than the width of the beam so that it does not rigidly constrain the test beam. The deflection guide is thus allowed to float in the span between the locating brackets. The apparatus may further include a mechanical cycle counter for counting the revolutions or cycles of the lathe device.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein.

DESCRIPTION OF THE PREFERRED EMBODIMENT

Figure 1:
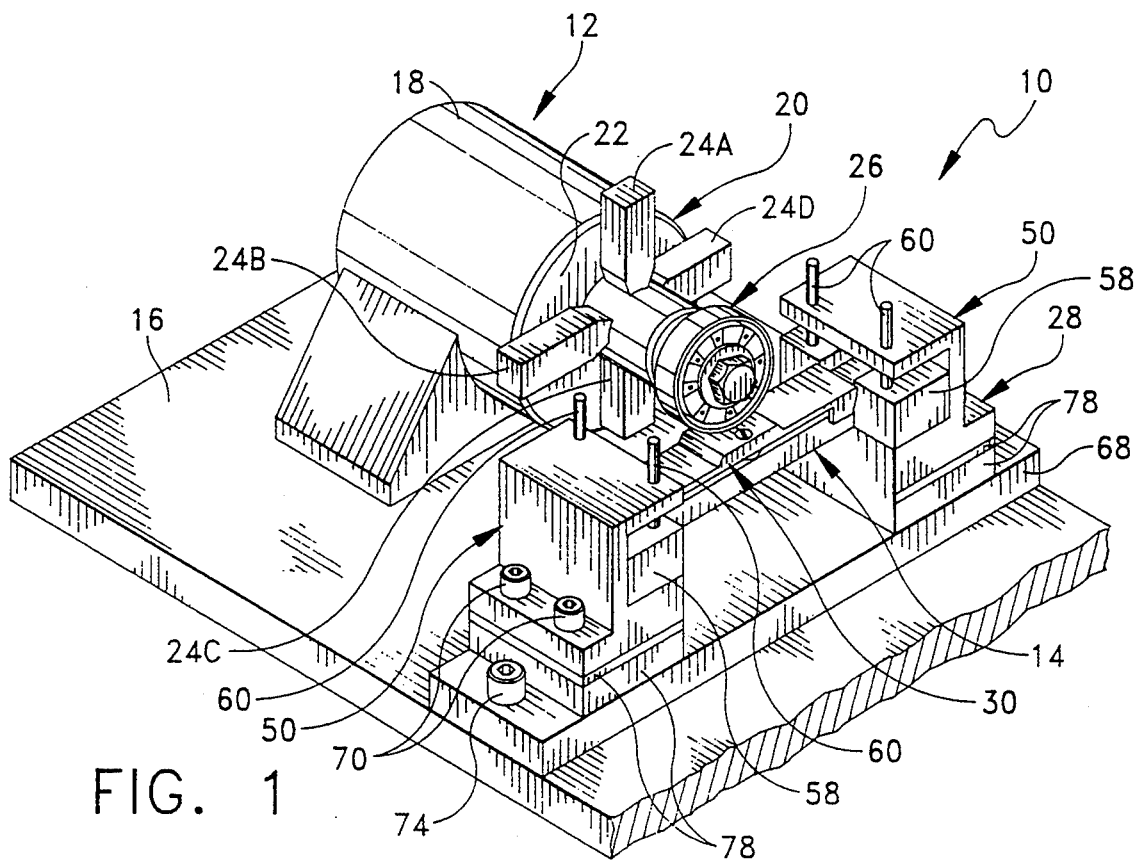
FIG. 1 is a perspective view of the apparatus of the instant invention as mounted on a small lathe device.

Referring now to the drawings, the apparatus of the instant invention is illustrated and generally indicated 10 in FIGS. 1 and 4–7. As will hereinafter be more fully described, apparatus 10 is operable in conjunction with a conventional lathe device generally indicated at 12 (FIG. 1). Apparatus 10 utilizes the eccentric rotary movement of lathe 12 to impart a cyclical flexive force to a rectangularly cross-section test beam generally indicated at 14.

Lathe device 12 includes a supporting base structure 16, a motor 18 having a rotatable shaft (not shown), and a chuck assembly generally indicated at 20 for mounting items to be rotated. Chuck assembly 20 includes a base plate 22 and four jaws 24A, 24B, 24C and 24D. In this connection, jaws 24 are slidably adjustable with respect to plate 22 for purposes of mounting a shaft in offset relation with the axis of rotation of the motor shaft.

Mounting a shaft in an offset relation causes the shaft to rotate in an eccentric pattern around the motor shaft axis. The particular construction details of chuck assembly 20 are conventional in the art, and therefore they will not be described in detail.

Figure 2:
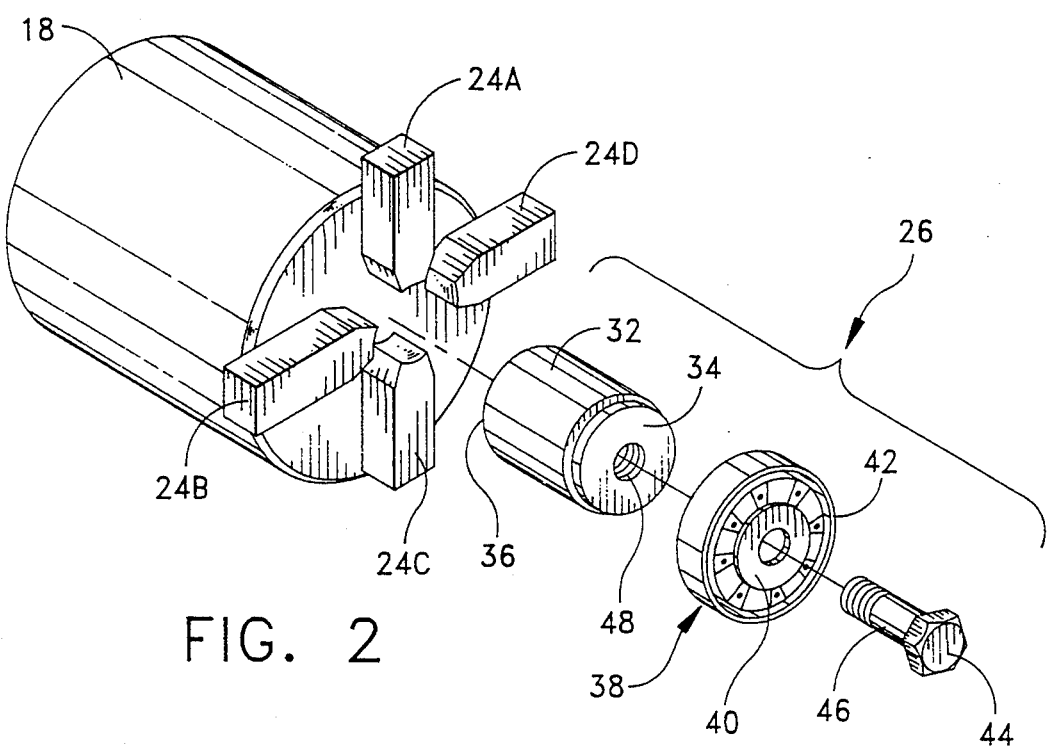
FIG. 2 is an exploded assembly view of the roller bearing assembly and pintle mounted in the chuck.

Apparatus 10 includes a bearing apparatus generally indicated at 26 (FIG. 2), a support structure generally indicated at 28 for supporting and caging test beam 14, and a flexible deflection guide generally indicated at 30 for flexing beam 14 at a predetermined point. Bearing apparatus 26 is mountable in jaws 24 as illustrated in FIG. 1. Bearing apparatus 26 consists of a cylindrical pintle generally indicated at 32 having first and second ends 34, 36 respectively, and a roller bearing assembly generally indicated at 38 axially mounted on first end 34 of pintle 32. Roller bearing assembly 38 is conventional in construction having inner and outer races 40, 42 respectively, and a plurality of roller balls 43 received in the raceway formed therebetween. Roller bearing assembly 38 is mounted to pintle 32 by means of a bolt 44 having a threaded shaft 46 which is passed through inner race 40 and into a threaded bore 48 in first end 34 of pintle 32. Second end 36 of pintle 32 is mounted in jaws 24 of chuck assembly 20 in a conventional manner. It is pointed out that jaws 24A and 24C are positioned in offset relation for eccentric rotation of bearing apparatus 26. (See FIGS. 4–7).

Figure 3:
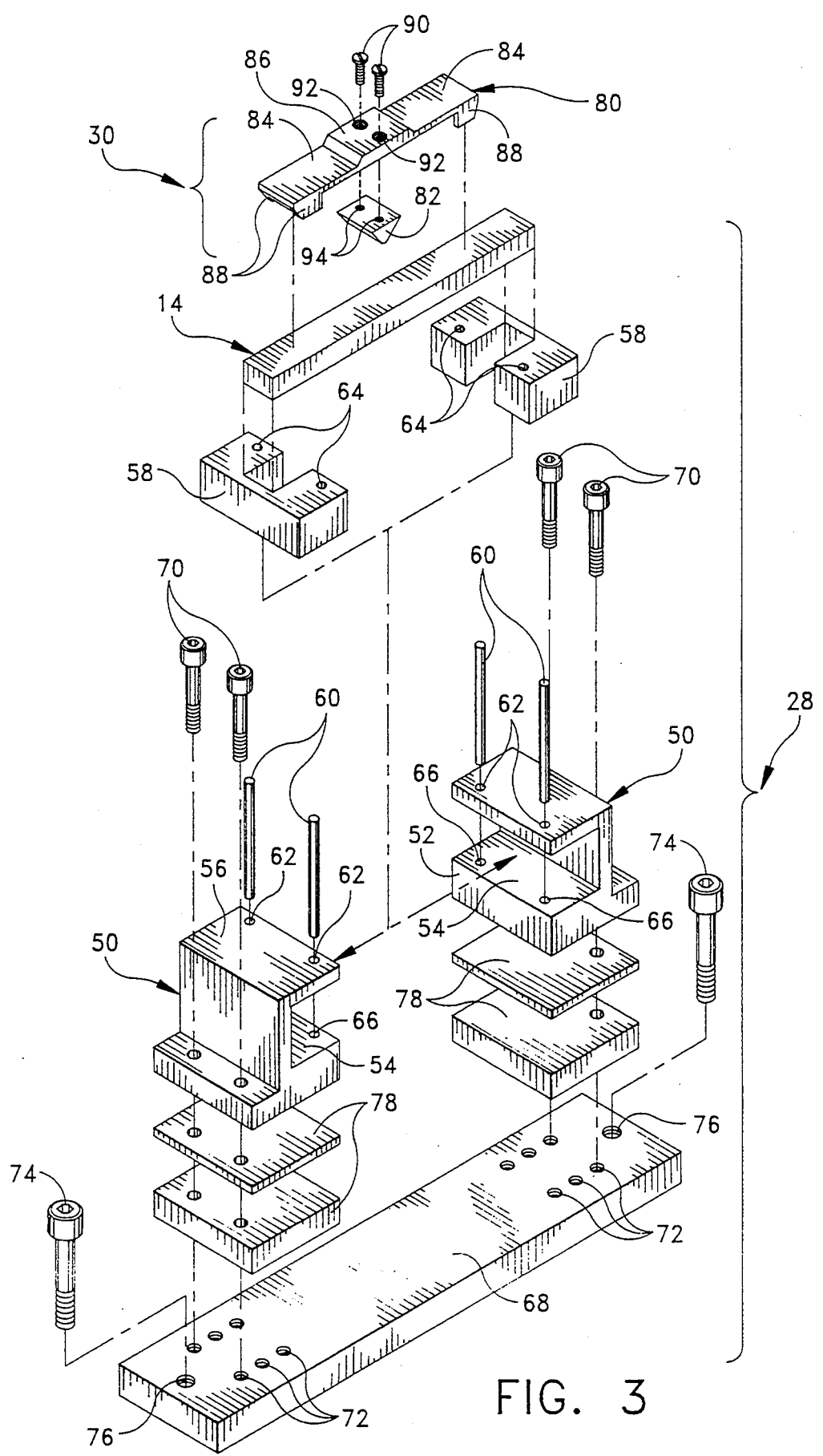
FIG. 3 is an exploded assembly view of the support structure for the supporting and caging the test beam.

Support structure 28 (FIG. 3) includes two locating brackets generally indicated at 50 for rigidly supporting the ends of the test beam 14. Locating brackets 50 include a base portion 52 having a supporting surface 54 and a flange 56 which overhangs supporting surface 54. Supporting structure 28 further includes two U-shaped guide blocks 58 which are received on supporting surface 54 for caging movement of the test beam, i.e., for preventing horizontal movement of beam 14 during testing. Guide blocks 58 are secured to locating brackets 50 by rods 60 which pass through openings 62 in flange 56, openings 64 in guide blocks 58 and into bores 66 in supporting surface 54. Beam 14 is received in the U-shaped notch formed by guide blocks 58 and is supported at each end on supporting surface 54 of locating brackets 50. However, it is pointed out that guideblocks 58 do not rigidly constrain test beam 14 along any face thereof. Locating brackets 50 are mountable on a bed plate 68 by means of threaded bolts 70. Bed plate 68 includes a plurality of sets of mounting bores 72 for positioning locating brackets 50 at various locations. Bed plate 68 is mountable on base 16 of lathe device 12 by threaded bolts 74 which pass through openings 76. In order to position beam 14 at an appropriate height for cyclic engagement of bearing 38, shims 78 can be positioned beneath locating brackets 50. Locating brackets 50, guide blocks 58, bed plate 68 and shims 78 are preferably fashioned from sturdy metal, such as steel.

Deflection guide 30 (FIG. 3) comprises a resilient body portion generally indicated at 80, and a wedge shaped impeller element 82 for engaging beam 14 at a predetermined point. Body portion 80 is preferably fashioned from a synthetic resin material to provide the required resiliency. Body portion 80 includes first and second symmetrical end portions 84 for supporting impeller element 82 above 14 beam, and further includes a central pressure plate 86 positioned between end portions 84. End portions 84 include downwardly extending spaced legs 88 which extend downwardly along the sides of beam 14. The legs 88 do not rigidly constrain the test beam 14 along the sides thereof. The outermost ends of said legs are machined at an angle so as not to cause interference with the guide blocks during a deflection cycle. Pressure plate 86 is slightly thicker than the remainder of body portion 80. Impeller element 82 is secured to the lower surface of pressure plate 86 by means of two screws 90 which pass through openings 92 in pressure plate 86 into bores 94 in impeller element 82. Impeller element 82 is preferably fashioned from a sturdy, non-abrasive metal, such as aluminum. Deflection guide 30 is positionable on top of beam 14 between locating brackets 50 with the impeller element 82 in confronting relation with the upper surface of test beam 14. The upper surface of deflection guide 30 is disposed normally to the plane of rotation of the roller bearing assembly 38. Accordingly, when bearing 38 makes cyclical contact with deflection guide 30, impeller element 82 contacts test beam 14 and flexes test beam 14 at a mid-point thereof. Deflection guide 30 has a lengthwise span which is slightly shorter than the distance between the inner faces of guide blocks 58. The shorter length provides a tolerance that allows deflection guide 30 to float in the span, i.e., there is no rigid constriction to movement. Further, the spaced feet 88 at each end of deflection guide 30 are spaced apart by a width which is slightly greater than the width of the beam 14.

Figure 4:
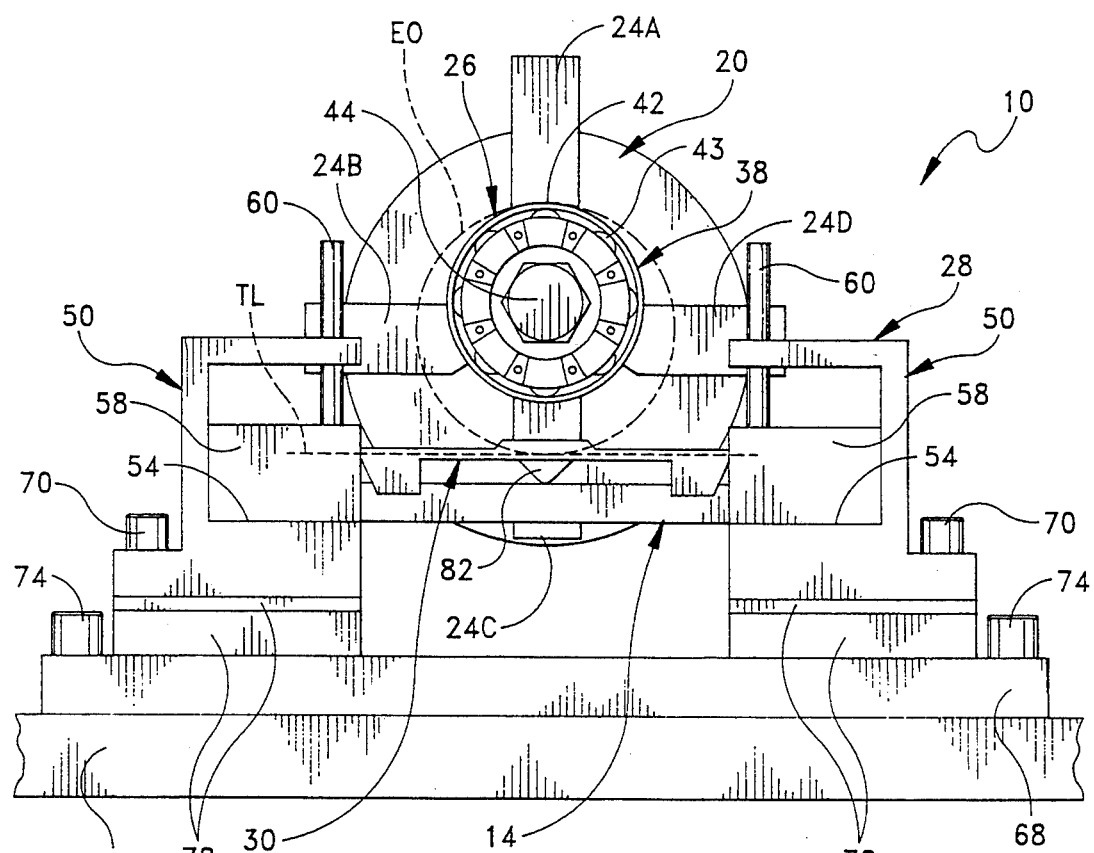
FIG. 4 is a front view of the apparatus with the roller bearing assembly mounted in offset relation in the chuck.
Figure 5:
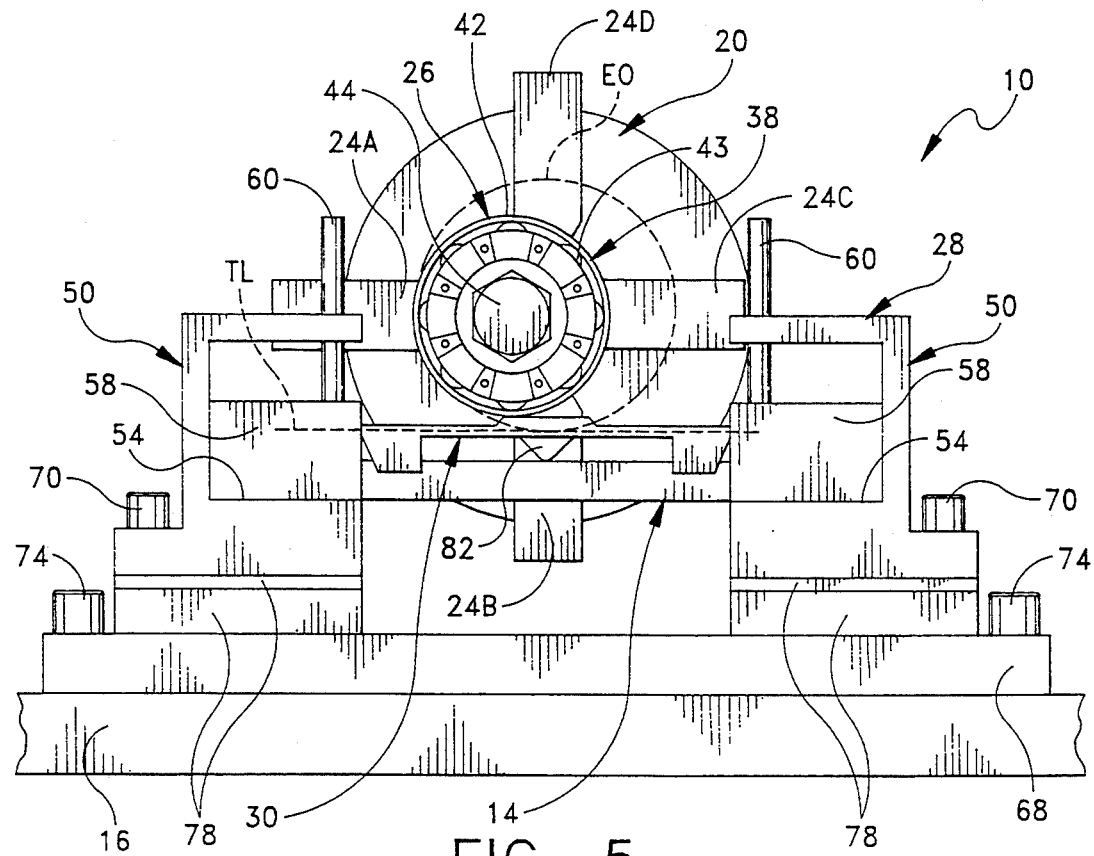
FIGS. 5–7 are further front views illustrating the eccentric rotation of the roller bearing assembly and resulting deflection of the test beam.
Figure 6:
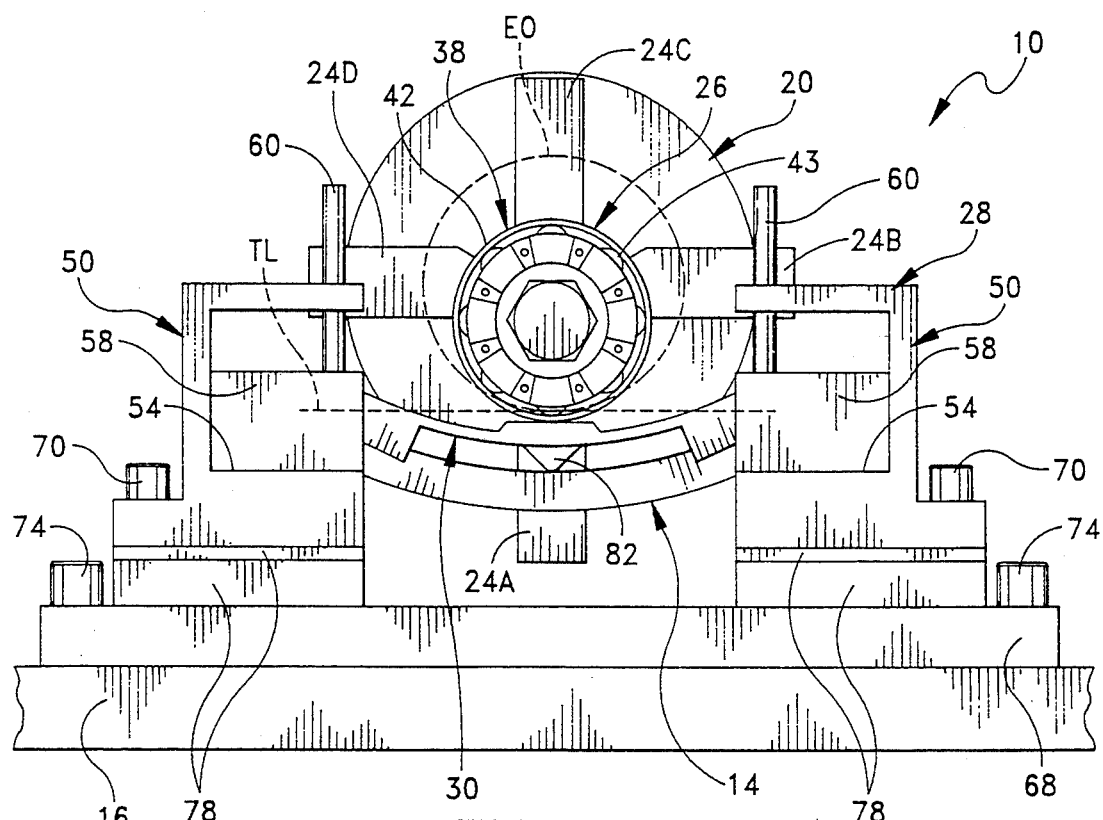
Figure 7:
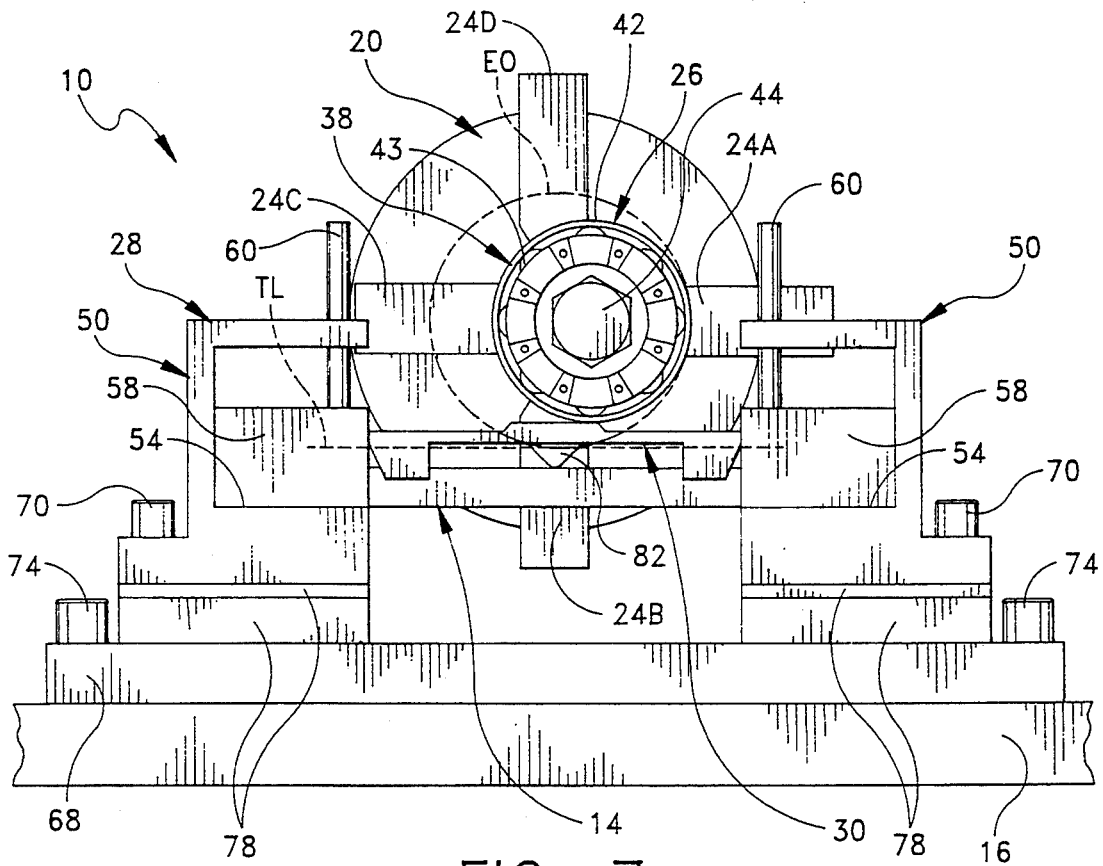

Referring now to FIGS. 4–7, the eccentric counter-clockwise rotation of roller bearing assembly 26, and resulting flexure of beam 14 is illustrated in ninety degree intervals. In this regard, FIG. 4 shows bearing 38 at a top center position, FIG. 5 shows bearing 38 at ninety degrees left of center with outer bearing race 42 making initial contact with pressure plate 86 of deflection guide 30, FIG. 6 shows bearing 38 at bottom center position with beam 14 fully deflected, and FIG. 7 shows bearing 38 at ninety degrees right of center. It can be seen that continuous eccentric rotation of bearing 38 will cause beam 14 to be cyclically flexed. Outer race 42 rotates with respect to gripping bar 32 during contact thus preventing fretting of pressure plate 86 and/or the surface of outer race 42 due to friction. It will be appreciated that the support surfaces 54 formed on locating brackets 50 provide fixed bearing support in directions normal to a reference line TL tangential to the excentric orbit EC of the outer race 42 of bearing assembly 38. This support instrumental in simulating three-point flexure of test beam 14.

Figure 8:
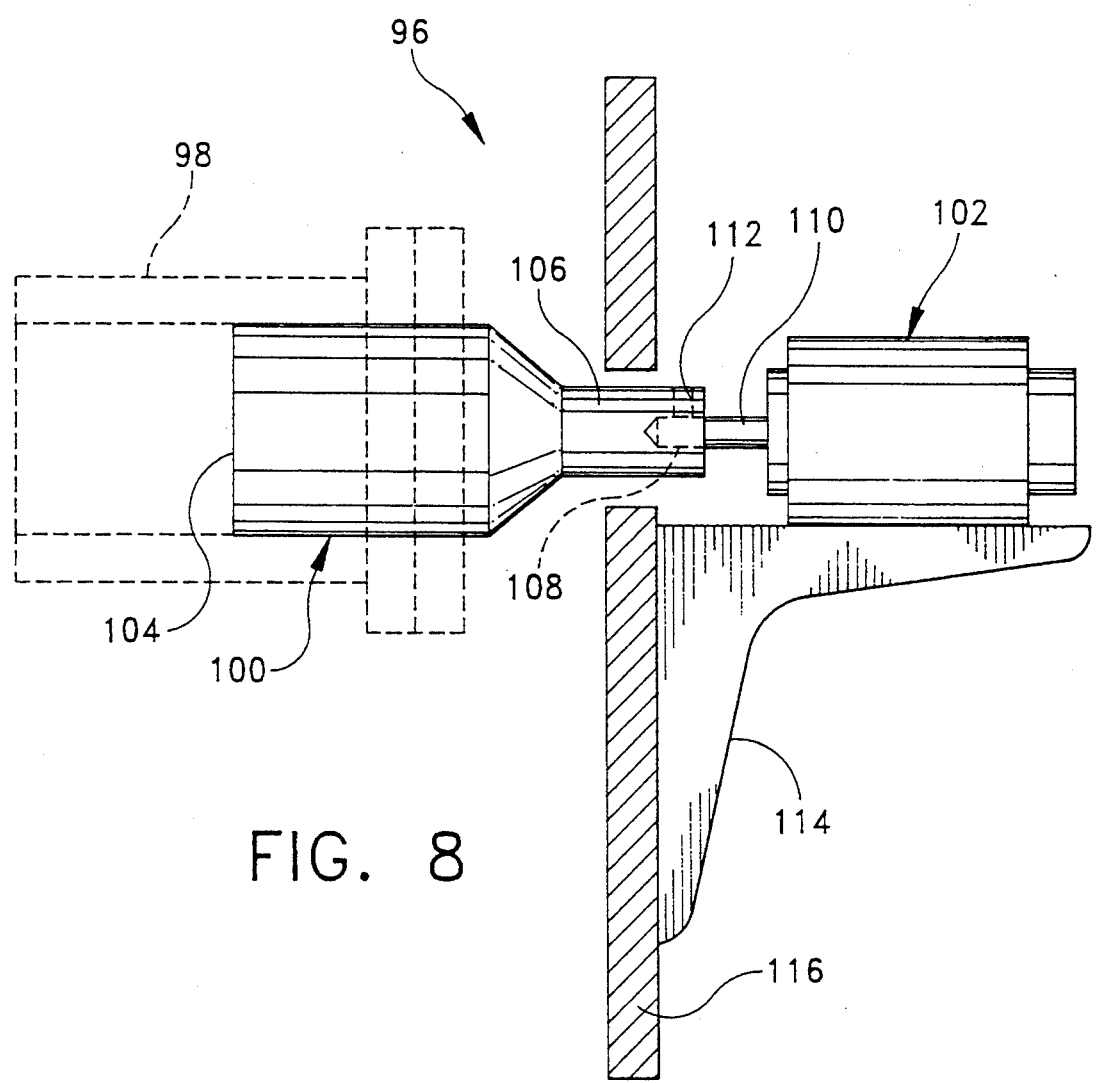
FIG. 8 is an elevational view of a counting apparatus mounted to the tail stock of the lathe device.

Referring now to FIG. 8, the preferred form of apparatus 10 further includes apparatus generally indicated at 96 for counting the revolutions or cycles of lathe device 12. The lathe device 12 further includes a tail stock 98 (shown in broken lines) which rotates at the same rate as chuck assembly 20. Counting apparatus 96 comprises a cylindrical adapter shaft generally indicated at 100 and a mechanical cycle counter generally indicated at 102. Adapter shaft 98 includes a first end 104 adapted to be received into tail stock 98 for rotation therewith. The second end 106 includes an axial bore 108 (shown in broken lines) which is adapted to receive the shaft 110 of mechanical cycle counter 102. A set screw 112 (shown in broken lines) is provided for securing shaft 110 within the bore 108. The construction specifics of mechanical cycle counter 102 are conventional in the art and will not be described further. Cycle counter 102 is preferably mounted on a bracket 114 which is secured to a wall 116 of a housing portion of lathe device 12.

Accordingly, it can be seen that the instant invention provides unique and effective apparatus 10 for conducting cyclical flexure testing of a test beam 14. While apparatus 10 is specifically adapted for a three-point flexure test, it is to be understood that support structure 28 and deflection guide 30 could be easily adapted to conduct fatigue tests on beams supported in different manners, such as a cantilevered beam. Apparatus 10 is easily set up and requires no specialized knowledge for operation. Bearing apparatus 26 is adapted for mounting in the jaws 24 of a chuck assembly 20 wherein beam 14 is supported in a supporting structure 28. The supporting structure and deflection guide are specially constructed and dimensioned so that the test beam and deflection guide are not rigidly constrained along any face thereof. The resilient deflection guide 30 is thus operative for imparting a flexive force to a mid-point of supported beam 14 without introducing any friction related fatigue. For these reasons, the instant invention is believed to represent a significant advancement in the art.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. Apparatus for performing beam flexure tests upon a rectangularly cross-section test beam comprising:

rotational drive apparatus including a rotating output shaft which is adapted to securely hold a pintle in eccentric relation to said rotating output shaft;

a roller bearing assembly including of inner and outer races, said roller bearing assembly being mounted to the pintle;

a flexible deflection guide postionable on said test beam, said deflection guide including upper and lower faces and an impeller element at a mid-point of said lower face;

means for rigidly supporting first and second ends of the test beam;

means for caging the test beam and the deflection guide relative to the eccentric orbit of the roller bearing assembly; and said means for caging being so constructed and arranged to maintain said test beam and said deflection guide in parallel stacked relationship, with the impeller element of the deflection guide in confronting relation with an upper surface of the test beam, said upper face of said deflection guide being disposed normally to the plane of rotation of said roller bearing assembly and inside the eccentric orbital path of said roller bearing assembly wherein engagement of the outer race of the roller bearing assembly with the upper face of the deflection guide will flex the deflection guide and through the impeller element flex the test beam at a mid-point thereof, said means for caging being so constructed and arranged so that said test beam and said deflection guide are not rigidly constrained along any face thereof except by said means for caging serving to provide fixed bearing support to ends of said test beam in directions normal to a reference line tangential to said eccentric orbit of the roller bearing assembly, whereby said apparatus is operative for simulating a three-point flexure of a beam.

2. The apparatus of claim 1 wherein said means for supporting comprises two locating brackets mountable in spaced relation for supporting the ends of the test beam.

3. The apparatus of claim 2 wherein said caging means comprises U-shaped guide blocks mountable on said locating brackets.

4. The apparatus of claim 1 wherein said deflection guide has first and second end portions, which support said impeller element in confronting relation with the upper face of said test beam.

5. The apparatus of claim 4 wherein said end portions includes opposing side flanges which extend downwardly along the sides of said beam.

6. The apparatus of claim 4 wherein said deflection guide has an increased thickness pressure plate in a central portion thereof.

7. The apparatus of claim 1 wherein said deflection guide comprising a synthetic resin body portion including first and second end portions, and a center portion between said end portions, said deflection guide further comprising a metallic wedge-shaped impeller element secured to and extending downwardly from a lower surface of said center portion for engagement with a mid-point of said test beam, said end portions supporting said impeller element in confronting relation with the upper surface of said test beam.

8. The apparatus of claim 1 further comprising a counting device for counting a number of rotations of said rotational drive.

* * * * *